United States Patent
Newman

(10) Patent No.: US 6,524,297 B1
(45) Date of Patent: Feb. 25, 2003

(54) VEIN STABILIZER FOR VENOUS NEEDLE INSERTION

(75) Inventor: George H. Newman, Niceville, FL (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 09/851,174

(22) Filed: May 9, 2001

(51) Int. Cl.[7] .............................................. A61M 31/00
(52) U.S. Cl. ........................ 604/506; 604/304; 604/305
(58) Field of Search ................................. 604/304, 305, 604/306, 307, 308, 171, 174, 506, 507, 511

(56) References Cited

U.S. PATENT DOCUMENTS

| 4,324,237 A | * | 4/1982 | Buttaravoli | 128/214 |
| 4,596,560 A | * | 6/1986 | Simpson | 604/174 |
| 4,633,863 A | * | 1/1987 | Filips et al. | 128/165 |
| 4,709,695 A | * | 12/1987 | Kohn et al. | 128/132 |
| 4,834,802 A | * | 5/1989 | Prier | 128/327 |
| 4,988,341 A | * | 1/1991 | Columbus et al. | 604/306 |
| 5,000,741 A | * | 3/1991 | Kalt | 604/180 |
| 5,010,902 A | * | 4/1991 | Rambo et al. | 128/888 |
| 5,380,294 A | * | 1/1995 | Persson | 604/180 |
| 5,728,071 A | * | 3/1998 | Watson et al. | 604/180 |
| 5,776,106 A | * | 7/1998 | Matyas | 604/180 |

* cited by examiner

Primary Examiner—Manuel Mendez
(74) Attorney, Agent, or Firm—William G. Auton

(57) ABSTRACT

A disposable product used to stabilize rolling veins and bring small veins into position to facilitate needle insertion. Needle insertion is used for transfusions, to draw blood samples, and for variety of other medical necessities. Many patients have either/or both small veins or veins that roll under the skin. Either of these characteristics has the tendency to complicate the process of sticking the needle in. As a result of these characteristics in concert with the mental and physical discomfort described by several recipients of multiple needle stabs, and fact that these characteristics complicate the speed of providing IV emergency care in a moving ambulance, the invention was developed. Invention is a sterile wrapped flexible plastic performed pad with an elongated hole in the middle, and coated on the bottom with bandage type adhesive.

1 Claim, 3 Drawing Sheets

VEIN STABILIZER FOR VENOUS NEEDLE INSERTION

STATEMENT OF GOVERNMENT INTEREST

The invention described herein may be manufactured and used by or for the Government for governmental purposes without the payment of any royalty thereon.

BACKGROUND OF THE INVENTION

The present invention relates generally to bandages and medical treatment and more specifically to a disposable product to stabilize rolling veins and bring small veins into position to facilitate needle insertion.

The present invention relates generally to an improved hypodermic needle, and more particularly, to an improved apparatus for administration of intravenous fluids to the body, particularly under conditions previously thought to create difficulty in such administration.

According to present practice, intravenous fluids of many kinds are administered to patients by so-called percutaneous injection, that is, piercing the skin with a hollow needle inserted into the vein in the hand, arm, or elsewhere in the patient. A generally standardized system of intravenous tubes, connectors and needles has been manufactured and is commonly accepted by the medical community for this purpose. Under common conditions of use, existing systems are satisfactory; however, like other engineered systems and products, they are still capable of further improvement. Moreover, there are certain circumstances in which existing needles used for intravenous administration of medicines and other fluids are inadequate or disadvantageous.

Referring to a common situation, following serious injury, it may be desired to administer fluid to a patient intravenously. However, because of the nature of the injury, and the condition and/or the position of the patient, it is difficult to locate the veins or to pierce the vein in such a way that the needle is inserted fully into but does not pass through the vein. For this purpose, most needles have simply been too large and unwieldy, and hence, incapable of reliable insertion into veins, especially those that are constricted or collapsed, as is often the case following trauma or other medical emergency.

The task of constricting surface flesh for improving vein susceptibility for needle insertion is alleviated but the following U.S. Patents, the disclosures of which are incorporated herein by reference:

U.S. Pat. No. 4,767,407, Aug. 30, 1988, Hypodermic needle, catheter and method, Foran, Scot, U.S. Pat. No. 6,113,568, Sep. 5, 2000, Vein catheter for coaxial blood stream and use of a split needle for its introduction in a vein, Olaussen, U.S. Pat. No. 5,407,431, Apr. 18, 1995, Intravenous catheter insertion device with retractable needle, Botich, Michael J, Richard W, U.S. Pat. No. 6,077,244, Jun. 20, 2000, Catheter insertion device with retractable needle, Botich, Michael J., Oxnard, U.S. Pat. No. 6,033,385, Mar. 7, 2000, Safety vein syringe with retractable special needle, Liu, Wen-Neng, U.S. Pat. No. 5,916,175, Jun. 29, 1999, Biopsy needle appliance and inserting guide with adjustable sample length and/or needle cutting stroke, Bauer, U.S. Pat. No. 5,494,039, Feb. 27, 1996, Biopsy needle insertion guide and method of use.

The best reference cited above is the Foran Patent which shows an indwelling vein catheter assembly with concentric puncture needle and wing-like, laterally extending, flexible elements tangentially attached to the catheter body; these wing-like elements can be folded around the catheter body to form angularly offset gripping and guide means which assume safe and smooth insertion of the catheter into a vein, and in the unfolded position provide support and steadying means for the inserted catheter.

SUMMARY OF THE INVENTION

The present invention is a disposable product used to stabilize rolling veins and bring small veins into position to facilitate needle insertion. Needle insertion is used for transfusions, to draw blood samples, and for variety of other medical necessities. Many patients have either/or both small veins or veins that roll under the skin. Either of these characteristics has the tendency to complicate the process of sticking the needle in. As a result of these characteristics in concert with the mental and physical discomfort described by several recipients of multiple needle stabs, and fact that these characteristics complicate the speed of providing IV emergency care in a moving ambulance, the invention was developed.

Invention is a sterile wrapped flexible plastic performed pad with an elongated hole in the middle, and coated on the bottom with bandage type adhesive. It is an object of the present invention to stabilize veins and bring them into position and into a condition to facilitate needle insertion. It is another object of the invention to simplify emergency medical care.

These and many other objects and advantages of the present invention will be readily apparent to one skilled in the pertinent art from the following detailed description of a preferred embodiment of the invention and related drawings.

DETAILED DESCRIPTION OF THE PREFERRED EMBODIMENT

Figure 2:
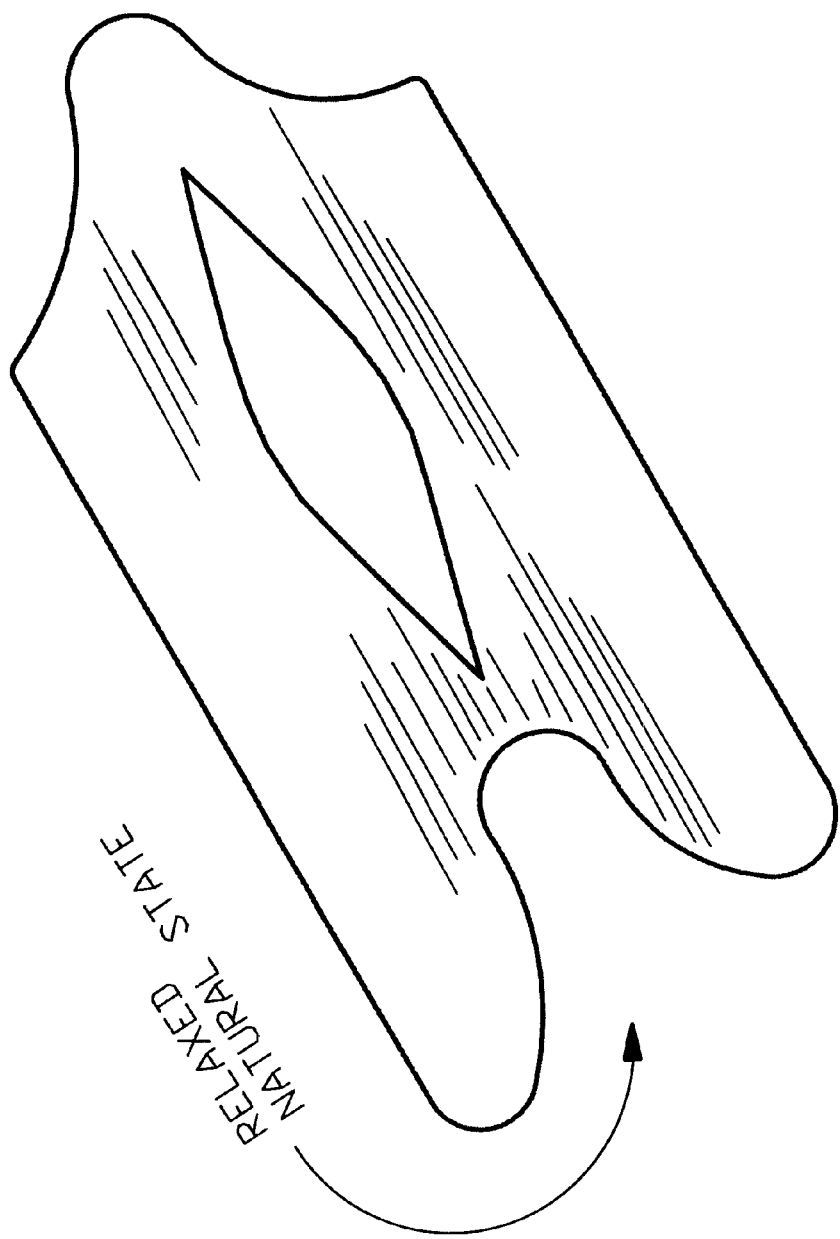
FIG. 2 is a plan view of the invention.
Figure 3:
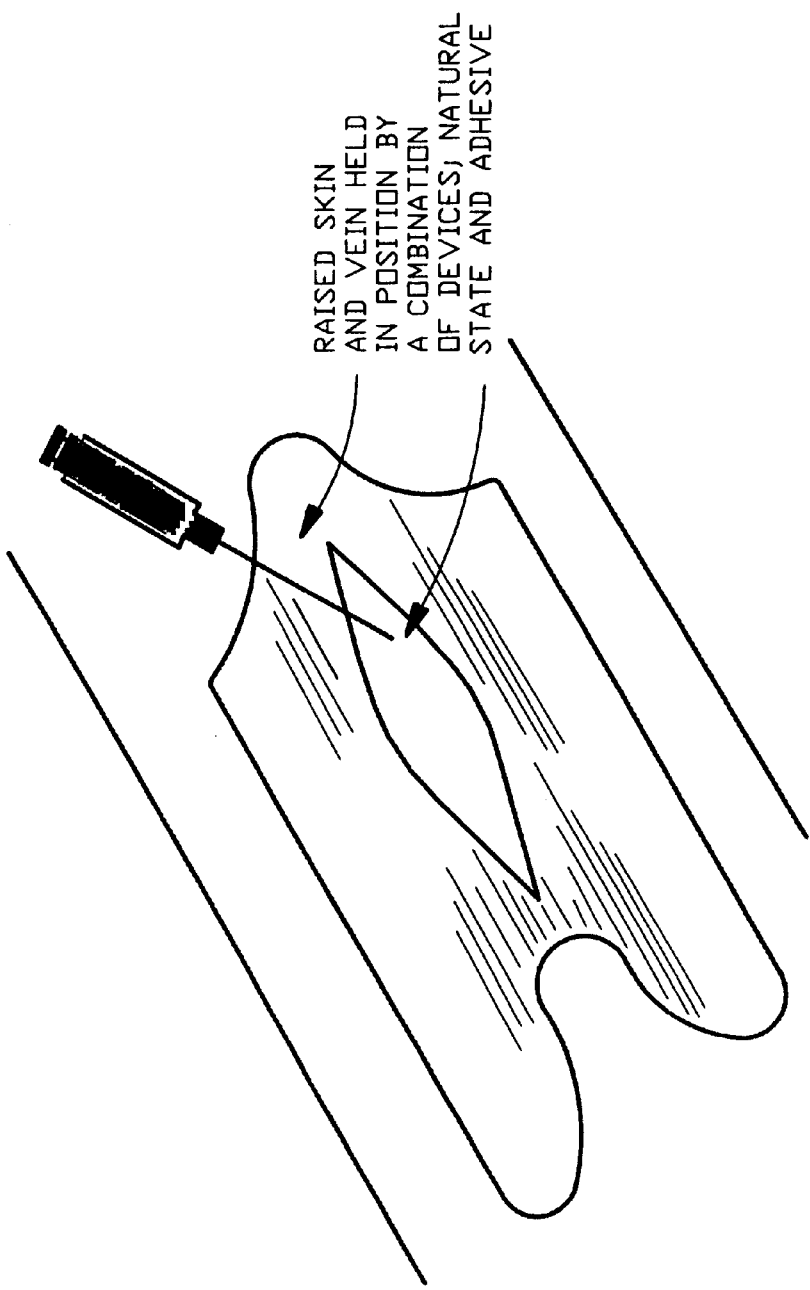
FIG. 3 shows the invention after it is in place and compressing a vein to facilitate raised skin and vein surface for needle insertion.

The present invention is a vein stabilizer process and system for facilitating venous needle insertion. The reader's attention is now directed towards FIGS. 1–3, which illustrate both the process and system as described below.

Figure 1:
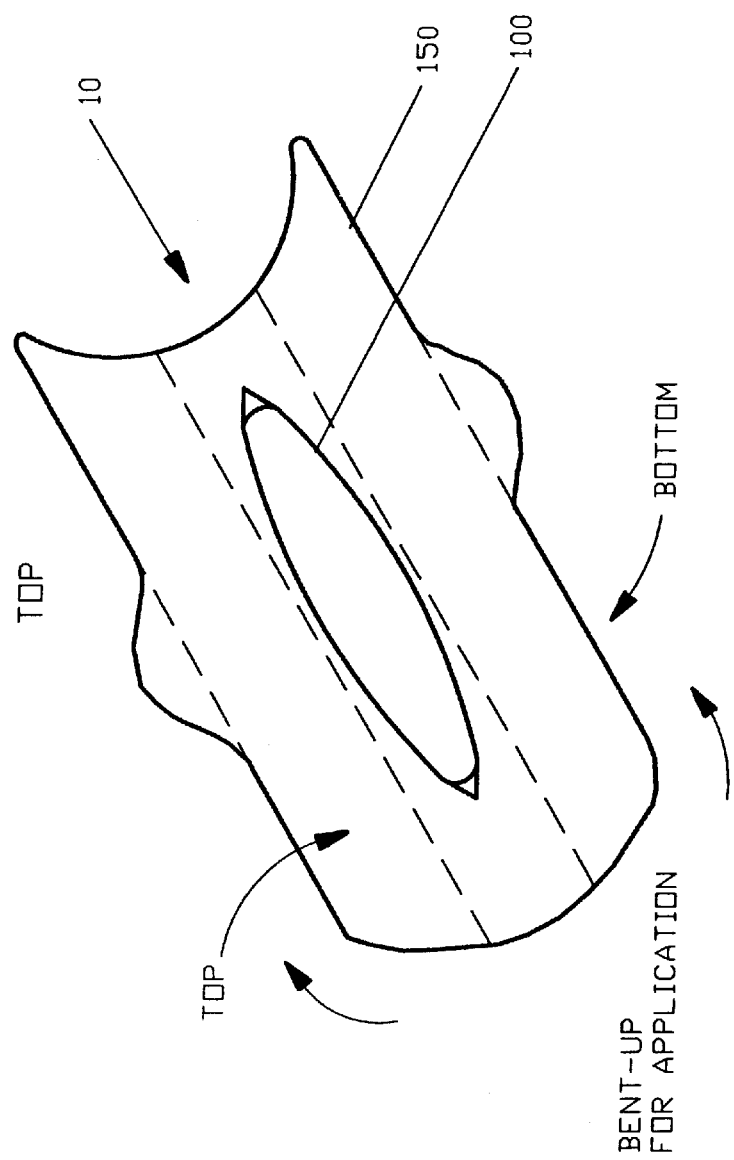
FIG. 1 is a view of the invention with the sterile wrap being removed.

The embodiment of the invention shown in FIG. 1 is a preformed adhesive bandage assembly 10 with a longitudinal aperture 100 which is placed over a surface area and aligned with a vein, and a sterile wrap 150 that is removed before application.

The six steps of the process are:

Step 1. The product is bent backwards.

Step 2. The sterile wrap is removed from product exposing adhesive.

Step 3. Product is aligned with vein/with vein running longitudinally under hole in product, and then product is pressed against skin.

Step 4. The product is released, which allows it to return to preformed position. This return to natural state allows skin/vein adhered to by product to be drawn up/above surrounding skin/limb.

Step 5. The product hole is covered by thin transparent membrane. This transparent membrane is sterile swabbed, followed by needle insertion through membrane/hole into vein. Note: Product can be manufactured/modified to allow shunt insertion and holding/stabilizing capability for long-term shunt use.

Step 6. Once the needle is withdrawn, the sterile tape/bandage can be applied directly over hole in product to reduce expected bleeding. Product can later be soaked or washed to cancel adhesive qualities, and product removed/peeled off.

Note that conventional materials and sterile bandage wrappers are used to make the elements of the present invention. Many suitable materials appear in the above-cited patents.

More importantly, the invention is a disposable product used to stabilize rolling veins and bring small veins into position to facilitate needle insertion. Needle insertion is used for transfusions, to draw blood samples, and for variety of other medical necessities. Many patients have either/or both small veins or veins that roll under the skin. Either of these characteristics has the tendency to complicate the process of sticking the needle in. As a result of these characteristics in concert with the mental and physical discomfort described by several recipients of multiple needle stabs, and fact that these characteristics complicate the speed of providing IV emergency care in a moving ambulance, the invention was developed.

Invention is a sterile wrapped flexible plastic preformed pad with an elongated hole in the middle, and coated on the bottom with bandage type adhesive.

While the invention has been described in its presently preferred embodiment it is understood that the words which have been used are words of description rather than words of limitation and that changes within the purview of the appended claims may be made without departing form the scope and spirit of the invention is its broader aspects.

What is claimed is:

1. A vein stabilizing process comprising the steps of:

flattening out a flexible plastic preformed pad which has a bottom side with an adhesive, said flexible plastic pad having a longitudinal aperture through which a needle may be inserted into a vein for hypodermic needle use, and said flexible plastic pad having a curved preformed body which is deflected prior to application;

applying the flattened preformed pad so that its longitudinal aperture is aligned with the vein and the adhesive connects the pad so that it holds the surrounding skin; and releasing the flexible plastic preformed pad so that it resumes its curved preformed body shape to press the skin and vein up into the longitudinal aperture to facilitate hypodermic needle use.

* * * * *